US00PP27816P3

(12) United States Plant Patent

Klemm et al.

(10) Patent No.: US PP27,816 P3

(45) Date of Patent: Mar. 28, 2017

(54) *DIANTHUS* PLANT NAMED 'KLEDG14177'

(50) Latin Name: ***Dianthus* sp.**
Varietal Denomination: KLEDG14177

(71) Applicant: Klemm+Sohn GmbH & Co. KG, Stuttgart (DE)

(72) Inventors: Nils Klemm, Stuttgart (DE); Martin Glawe, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 67 days.

(21) Appl. No.: 14/545,532

(22) Filed: May 18, 2015

(65) Prior Publication Data

US 2016/0014946 P1 Jan. 14, 2016

Related U.S. Application Data

(60) Provisional application No. 61/998,888, filed on Jul. 10, 2014.

(51) Int. Cl.
*A01H 5/02* (2006.01)

(52) U.S. Cl.
USPC ..... Plt./273

(58) Field of Classification Search
USPC ..... Plt./272, 273
See application file for complete search history.

*Primary Examiner* — Anne Grunberg

(74) *Attorney, Agent, or Firm* — James M. Weatherly; Barbara Campbell; Cochran Freund & Young, LLC

(57) ABSTRACT

A new *dianthus* plant named 'KLEDG14177' particularly distinguished by dark purple flowers with a dark center, small, dark green to blue leaves, and very good branching, is disclosed.

1 Drawing Sheet

Genus and species: *Dianthus* sp.
Variety denomination: 'KLEDG14177'.

BACKGROUND

The present invention comprises a new and distinct variety of *Dianthus*, botanically known as *Dianthus* sp. and hereinafter referred to by the variety name 'KLEDG14177'. 'KLEDG14177' is a selection that resulted from a cross pollination of the proprietary female *dianthus* line 'DSS 2009 0513' (unpatented) and the male *dianthus* line 'DSS 2008 0003' (unpatented).

In August 2010 the proprietary female *dianthus* line 'DSS 2009 0513' and the proprietary male *dianthus* line 'DSS 2008 0003' were cross pollinated in Stuttgart, Germany and seeds were obtained. The seeds were sown and plants were grown for evaluation. A plant line was selected in June 2011 in Stuttgart, Germany, and named 'KLEDG14177'. In June 2011, 'KLEDG14177' was first vegetatively propagated by vegetative cuttings. 'KLEDG14177' was found to reproduce true to type in successive generations of asexual propagation via vegetative cuttings in Stuttgart, Germany.

SUMMARY

The following are the most outstanding and distinguishing characteristics of this new variety when grown under normal horticultural practices in Stuttgart, Germany.

1. Dark purple flowers with a dark center;
2. Small, dark green to blue leaves; and
3. Very good branching.

DESCRIPTION OF THE PHOTOGRAPH

This new *Dianthus* plant is illustrated by the accompanying photograph, which shows the overall plant habit of the variety 'KLEDG14177' grown in a pot. The photograph is of a 10 to 12 week old plant in Stuttgart, Germany under greenhouse conditions in May 2013. The colors shown are as true as can be reasonably obtained by conventional photographic procedures.

DESCRIPTION OF THE NEW VARIETY

The following detailed description set forth the distinctive characteristics of 'KLEDG14177'. The data which define these characteristics were collected from asexual reproductions carried out in Stuttgart, Germany. Data was collected on four month old plants grown in a glass greenhouse in Stuttgart, Germany in March, 2014. Color references are to The R.H.S. Colour Chart of The Royal Horticultural Society of London (R.H.S.), 5$^{th}$ edition.

Classification:

*Family.*—Caryophyllaceae.
*Species.*—*Dianthus* sp.
*Common name.*—Garden carnation.
*Type.*—Spray type carnation.
*Parentage.*—Female: Proprietary *dianthus* line 'DSS 2009 0513'. Male: Proprietary *dianthus* line 'DSS 2008 0003'.

Propagation:

*Type.*—Vegetative stem cuttings.
*Time to produce a rooted young plant.*—About 20 days.
*Root description.*—White, small, well-branched.
*Rooting habit.*—Lanceolate.

Plant description:

*Plant form.*—Bushy, potted and garden plant.
*Plant height.*—10.0 cm.
*Plant diameter or spread.*—18.0 cm.

Lateral branches:
*Stem*.—Solid.
*Length*.—6.0 cm.
*Diameter*.—1.5 cm.
*Number of internodes per stem*.—3 to 4.
*Internode length*.—0.6 cm.
*Node length*.—0.3 cm.
*Node diameter*.—0.3 cm.
*Texture*.—Smooth.
*Color*.—RHS 137B.

Foliage description:
*Arrangement*.—Opposite.
*Length*.—5.0 cm.
*Width*.—0.2 cm.
*Shape*.—Lanceolate.
*Apex*.—Acute.
*Base*.—Obtuse.
*Margin*.—Entire.
*Texture*.—Upper and lower surfaces: Smooth.
*Color*.—Immature and mature leaves: Upper surface: RHS 137B. Lower surface: RHS 137C.
*Venation pattern*.—Parallel.
*Venation*.—RHS 137D.

Flower description:
*Flower type and habit*.—Single, round.
*Flower position*.—Slightly above the foliage.
*Fragrance*.—Absent.
*Natural flowering season*.—Spring to autumn.
*Flower longevity*.—6 to 8 days.
*Number of flowers per spray*.—3 to 4.
*Flower buds*.—Length: 1.8 cm. Diameter: 0.5 cm. Shape: Tall cylinder to cylindrical. Color: RHS 137C. Extrusion of the styles at bud stage: Absent.
*Corolla*.—Quantity of petals/arrangement: 5, round. Corolla height: 0.5 cm. Petal length: 3.0 cm. Petal width: 1.4 cm. Petal shape: V-shaped. Petal apex: Obtuse. Petal base: Cuspidate. Petal margin: Serrate, depth is medium. Petal texture: Upper and lower surfaces: Smooth. Petal color: Immature: Upper surface: Main color is RHS N74A and the secondary color in the eye is RHS 64A. Lower surface: RHS N74C. Mature: Upper surface: Main color is RHS N74A and the secondary color in the eye is RHS 61A. Lower surface: RHS N74C. Calyx: Quantity of sepals/arrangement: 5, single. Calyx height: 2.0 cm. Calyx diameter, at the apex: 0.5 cm. Shape: Campanulate. Sepal apex shape: Acute. Sepal texture: Upper and lower surfaces: Smooth. Sepal color: Upper surface: RHS 137C. Lower surface: RHS 137D. Epicalyx: Position of the outer lobes in relation to the calyx: adpressed. Apex shape of inner and outer lobes: Acute. Length: 0.7 cm.

Peduncles:
*Length*.—6.5 cm.
*Diameter*.—1.0 cm.
*Strength*.—Moderate.
*Texture*.—Smooth.
*Color*.—RHS 136B.

Reproductive organs:
*Stamens*.—Quantity: Greater than 5. Filament length: 1.0 cm. Filament color: RHS 75C. Anther length: 0.15 cm. Anther diameter: 0.08 cm. Anther color: RHS 75B. Pollen amount: Moderate.
*Pistils*.—Quantity: 1. Pistil length: 0.8 cm. Style length: 0.1 cm. Style color: RHS 76D. Stigma shape: Filamentous. Stigma color: RHS 72A. Ovary size: 0.4 cm. Ovary shape: Ovate. Ovary color: RHS 139D. Ovary texture: Smooth. Fruits/seeds: None observed.

Disease and insect/pest resistance: No special observations were made.

COMPARISON OF WITH PARENTAL LINES AND KNOWN VARIETY

When 'KLEDG14177' is compared to the female and male parental lines, the following differences are noted in Table 1:

TABLE 1

Comparison with Parental Lines

| Trait | Variety 'KLEDG14177' | Female parent 'DSS 2009 0513' | Male Parent 'DSS 2008 0003' |
|---|---|---|---|
| Flower color | Dark purple with a dark center | Lilac | White |
| Branching | Very good | Good | Less branching |

When 'KLEGD14177' is compared to the commercial line 'Kahori' (patent status unknown), the following differences are noted in Table 2:

TABLE 2

Comparison with Similar Variety

| Trait | Variety 'KLEDG14177' | Commercial line 'Kahori' |
|---|---|---|
| Flower color | Dark purple with a dark center | Purple and blue |
| Color of foliage | Dark green to blue | Green |
| Size of leaves | Small | Medium |

We claim:

1. A new and distinct variety of *Dianthus* plant named 'KLEDG14177' as illustrated and described herein.

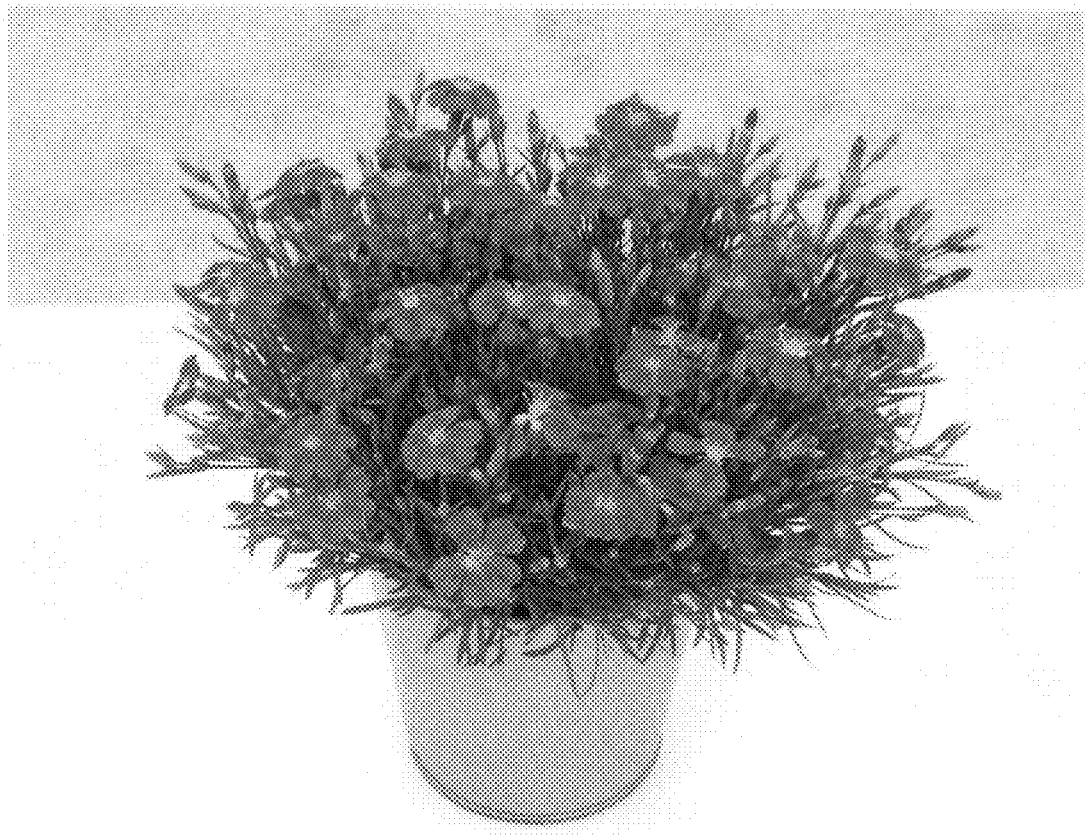

* * * * *